United States Patent [19]

Ahn et al.

[11] Patent Number: 5,530,541
[45] Date of Patent: Jun. 25, 1996

[54] ATOMIC ABSORPTION APPARATUS USING A PHASE-MODULATED LIGHT BEAM

[75] Inventors: Charles H. Ahn; Malcolm R. Beasley, both of Palo Alto, Calif.; Steven J. Benerofe, Rye Brook, N.Y.; Martin M. Fejer, Palo Alto, Calif.; Robert H. Hammond, Los Altos, Calif.; Marc D. Levenson, Saratoga, Calif.; Weizhi Wang, Mountain View, Calif.; Marc D. Levenson, Ssratoga

[73] Assignee: Board of Trustees of the Leland Stanford Junior University, Stanford, Calif.

[21] Appl. No.: 396,215

[22] Filed: Feb. 28, 1995

[51] Int. Cl.⁶ .................................................. G01N 21/39
[52] U.S. Cl. ............................................................ 356/311
[58] Field of Search ...................... 356/311, 312, 356/315, 316, 317, 318

[56] References Cited

U.S. PATENT DOCUMENTS 3,938,058  2/1976  Yamamoto .............................. 372/20

*Primary Examiner*—F. L. Evans
*Attorney, Agent, or Firm*—Lumen Intellectual Property Services

[57] ABSTRACT

An atomic absorption apparatus using a laser for producing a light beam having a characteristic frequency f, typically ranging from several MHz to several GHz, and a characteristic polarization for measuring the absorption of that light beam by atoms of interest. The apparatus has a modulator to generate a modulating signal to modulate the characteristic frequency f and produce a phase-modulated light beam. The apparatus includes a domain where the specific atoms are located. This domain is positioned in the path of the phase-modulated light beam such that the phase-modulated light beam encounters the specific atoms when passing through the domain and some of the specific atoms absorb a portion of the phase-modulated light beam. Typically, the domains containing the atoms of interest include process chambers for vacuum coating, ion milling, sputtering, mass spectroscopy vapor coating or deposition, and the like. The amount of light absorbed depends on the motion of the atoms relative to the phase-modulated light beam.

19 Claims, 2 Drawing Sheets

ATOMIC ABSORPTION APPARATUS USING A PHASE-MODULATED LIGHT BEAM

BACKGROUND

1. Field of the Invention

The present invention relates to the field of monitoring devices using the effect of atomic absorption for quantifying particles of interest, and in particular to an atomic absorption monitor using a frequency-modulated light beam generated by a laser for ascertaining the presence and movement-related parameters of such particles.

2. Description of Prior Art

Monitors for quantifying particles involved in processes such as thin film deposition, evaporation, sputtering, laser ablation, ion milling, and secondary ion mass spectroscopy are crucial to many areas of technology. Particularly strict demands are placed on such monitors in supervising thin film deposition processes involving high temperatures, pressures, and throughputs. Ion milling and secondary ion mass spectroscopy pose no lesser monitoring challenges, especially with regard to sensitivity. To satisfy these stringent requirements, the devices need to be robust, versatile, accurate, sensitive, and they should require little or no maintenance.

In addition to detecting the quantity of the particles of interest, it is also important to determine other parameters related to their movement. For example, it is highly desirable to know how fast and in which direction a particle is moving. Such information helps to determine deposition rates, velocity profiles inside process chambers, sticking coefficients, and many other technical parameters.

Traditional rate monitors include quartz crystal monitors (QCM), quadrupole mass spectrometers (QMS), ion gauges, and electron impact emission spectrometers (EIES). Unfortunately, these monitors do not always have the requisite versatility or robustness for many applications. The monitors relying on a hot filament, including the QMS, ion gauge, and the EIES cannot be used in high-pressure applications such as sputtering. Also, when sputtering or other deposition processes are used to achieve high throughput, as is frequently done in the semiconductor industry, none of the above techniques, including the QCM technique, can be employed. The rapid coating of monitors under these conditions results in frequent downtime inside the vacuum system for cleaning operations. Such interruptions are not economically feasible. In fact, for these two reasons, rate monitors are often non-existent today in commercial semiconductor sputtering applications.

Atomic absorption monitors offer considerable advantages over the traditional devices listed above. They do not need to be placed inside vacuum chambers and thus avoid being coated by the deposition material. This contributes to their overall low maintenance requirements. Atomic absorption devices are also highly element-specific, insensitive to extreme conditions such as high temperatures and pressures, and capable of tracking low and high deposition rates.

Many existing atomic absorption monitors use a hollow cathode lamp to emit a signal beam of a characteristic wavelength. This beam passes through a chamber, e.g., a deposition chamber, containing the particles of interest. The particles absorb a portion of the signal beam which depends on their density, absorption cross section, and the length of the region containing the said particles of interest. Upon emerging from the chamber the beam is intercepted by appropriate photo-electronic detection means (e.g., a photodiode) which converts it into an electrical signal. The intensity reduction due to absorption is computed from this detected signal. Deposition rates, material component ratios, and other parameters are then derived from this result in a straightforward way.

Unfortunately, such atomic absorption monitors experience problems due to the intrinsic instability and incoherence of the light source and detection means. Both have a tendency to drift with time. In applications involving slow deposition rates, deviations of 10% per hour of the evaporation signal are not uncommon. Moreover, random noise of the detection means adds instantaneous fluctuations to the drift. Under these conditions it is next to impossible to determine additional parameters related to the movement of the particles with any accuracy. Moreover, it is also difficult to use the rapidly spreading spatially incoherent beam of a conventional monitor in the case where the atoms are confined to a region with a large aspect ratio.

OBJECTS AND ADVANTAGES OF THE INVENTION

In view of the above, it is an object of the invention to provide an atomic absorption monitor which accurately compensates for drifts in light source and detecting means during operation without interruptions. Furthermore, the envisaged monitor is capable of determining movement-related parameters, e.g., velocity profiles, of the particles being measured.

Another object of the invention is to adapt such atomic absorption monitors for continuous feedback to adjust the particular process parameters one wishes to control.

Finally, it is an object of the invention to ensure that the atomic absorption monitor is versatile, highly sensitive, and requires little or no maintenance.

These and other objects and advantages will become more apparent after consideration of the ensuing description and the accompanying drawings.

SUMMARY OF THE INVENTION

The objectives of the invention are achieved by an atomic absorption apparatus using a laser, preferably a tunable laser, for producing a light beam having a characteristic frequency f and polarization, and measuring the absorption of that light beam by atoms of interest. This apparatus includes a laser for emitting the light beam, a modulating signal source, preferably a radio-frequency source, for generating and transmitting a modulating signal having a frequency larger than 50 MHz and an electro-optic modulator located downstream from the laser for receiving the light beam and the modulating signal. The choice of modulation frequency in frequency-modulation spectroscopy depends mainly on noise characteristics of the laser. Typically, a diode laser has a flat noise spectrum ranging from several MHz to several GHz, so frequencies in such a low noise region is preferably employed. However, for detecting atomic absorption with resonance width wider than 100 MHz, low frequency modulation, for example several MHz, results in small signal because the difference in absorption seen by the two sidebands generated by the modulator is small. There is no cut-off frequency for obtaining the absorption signal, but the signal decreases quadratically with the decrease of the modulation frequency when the modulation frequency is smaller than the resonance width. Choice of very high modulation, for example several GHz, then is high cost in the electronics devices including the electro-optic modulator. Preferably, modulation frequency is chosen from 50 MHz to 3 GHz.

The modulator uses the modulating signal to modulate the characteristic frequency f to produce a phase-modulated light beam. The apparatus also includes a domain where the specific atoms are located, and this domain is located in the path of the phase-modulated light beam such that the phase-modulated light beam encounters the specific atoms when passing through the domain and some of the specific atoms absorb a portion of the phase-modulated light beam. The amount of light absorbed depends on the motion of the atoms relative to the phase-modulated light beam. Finally, the apparatus also has a photodetection element for receiving the phase-modulated light beam emerging from the domain and converting it into an electrical signal. The photodetection element is preferably a photomultiplier tube or a photodiode.

The apparatus can include additional polarizing elements, such as half-wave plates, optical rotators, etc., to ensure proper polarization of the light beam before the latter enters the electro-optic modulator. In addition, the apparatus preferably also includes an isolating element located in the path of the light beam for preventing re-entry of the light beam into the laser as well as the entry of any stray light.

The domain in which the specific atoms are contained is preferably a closed chamber with a window for admitting the phase-modulated light beam and a window for allowing the phase-modulated light beam to exit. Typically, such chambers can include a vacuum coating chamber, an ion milling chamber, a sputtering chamber, a mass spectrometer chamber, a vapor coating chamber, or a chemical vapor deposition chamber.

The invention further discloses a method for measuring absorption of the light beam by the specific atoms. Deviation signals are used to determine the movement of specific atoms in the chamber. A detailed description of the apparatus and method, with reference to the attached drawing figures, is found below.

DESCRIPTION

Figure 1:
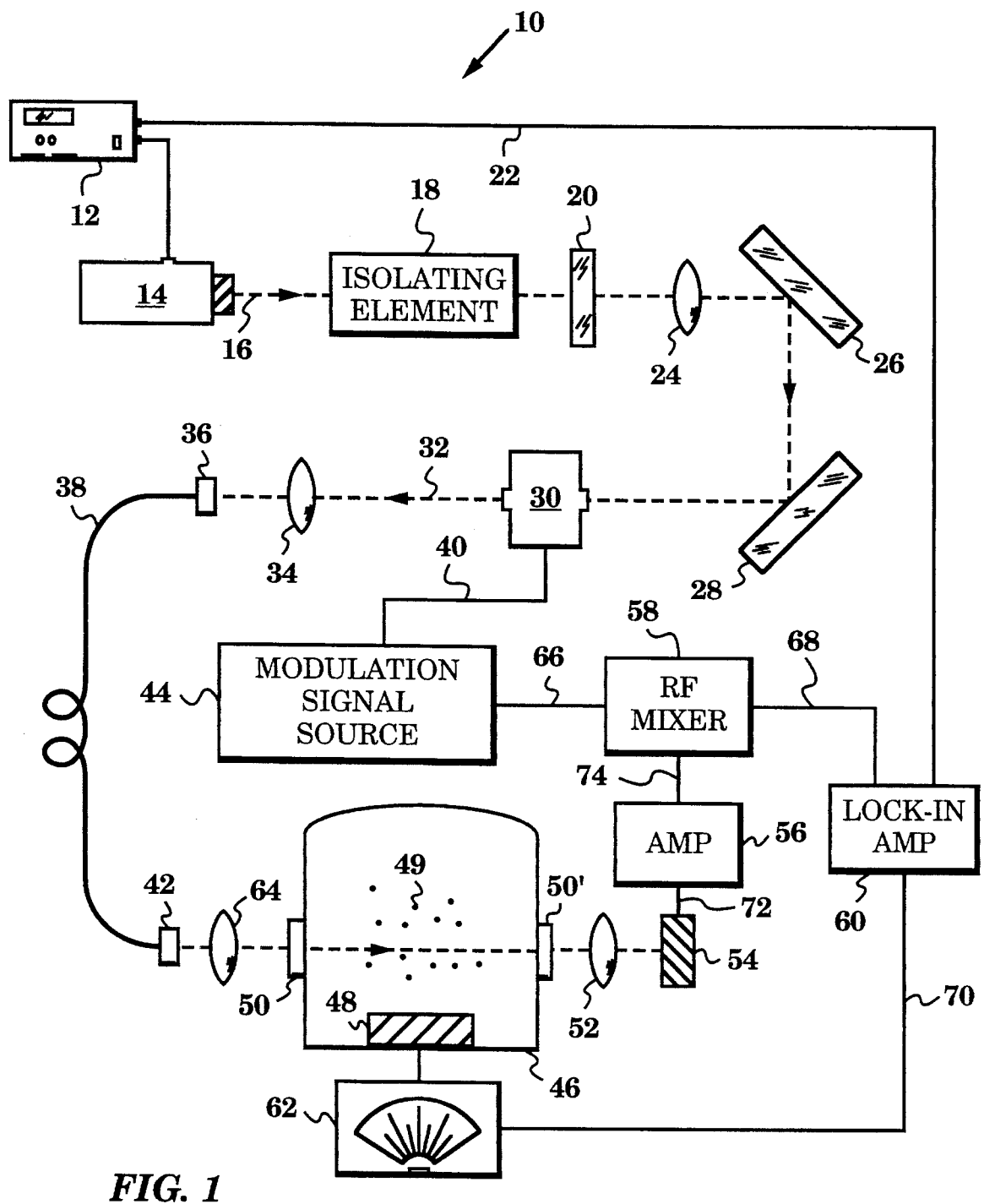
FIG. 1 is a block-schematic view of an atomic absorption monitor according to the invention.
Figure 2:
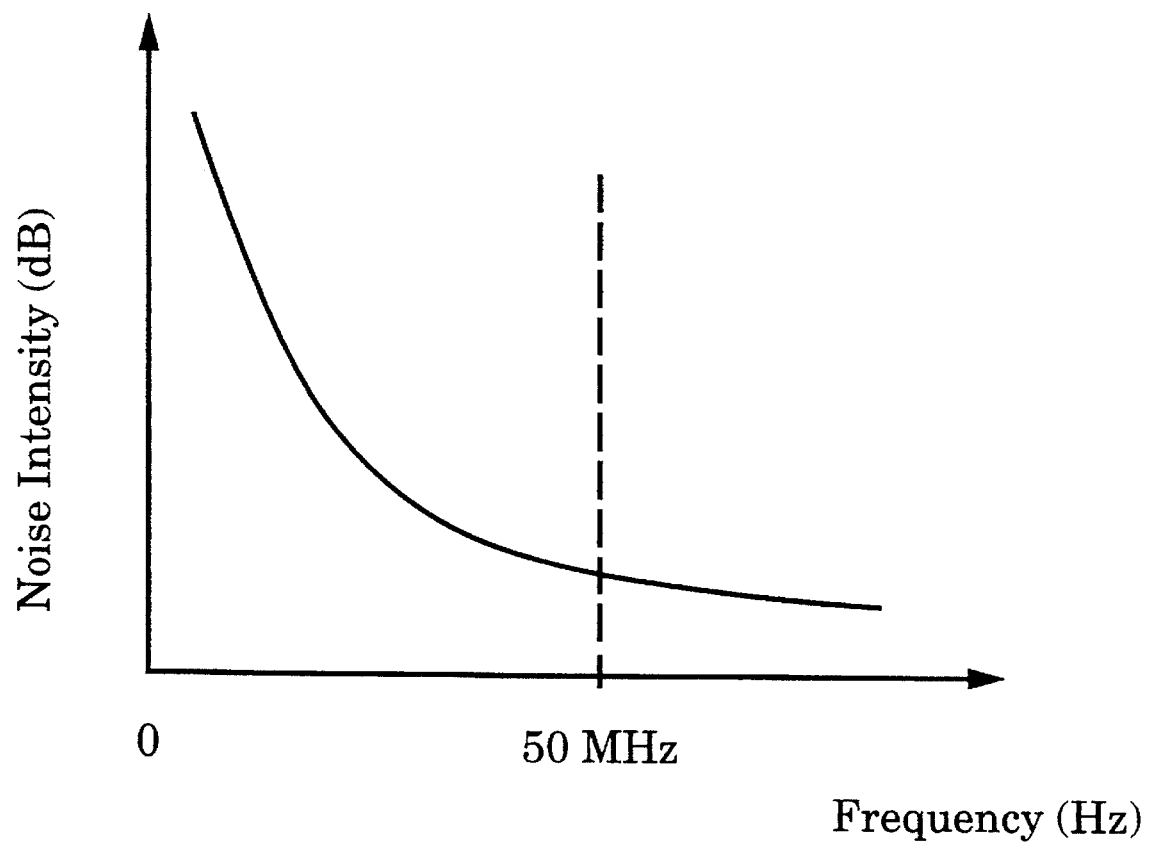
FIG. 2 is a graph showing the decrease in background noise as a function of frequency.

FIG. 1 illustrates a preferred embodiment of an atomic absorption apparatus 10 equipped with a laser 14. A control unit or function generator 12 is connected to laser 14. Generator 12 is a standard unit capable of generating various types of wave forms to activate laser 14. Preferably, laser 14 is a tunable laser, e.g., an external grating cavity diode laser. Typically, the tunable range is from 10 nm to 100 nm.

Laser 14 generates a light beam 16. An isolating element 18 is placed next to laser 14 in the path of light beam 16. Element 18 is a standard optical unit which prevents light beam 16 from being reflected back into laser 14 and degrading the quality of beam 16.

A polarization adjusting unit 20 capable of rotating the polarization of beam 16 is positioned beyond element 18 in the path of beam 16. In the present embodiment, unit 20 is a half-wave plate.

A focusing lens 24 and two mirrors 26 and 28 guide beam 16 from unit 20 to an electro-optic modulator 30. A modulation signal source 44 is connected by a transmission line 40 to modulator 30. Source 44 is capable of generating high-frequency electrical signals to control modulator 30. In particular, source 44 is a radio-frequency generator. In the present embodiment, source 44 is a sinusoidal wave generator at frequency of 450 MHz. Modulator 30 is a standard electro-optic unit which responds to electrical signals by modulating the phase of beam 16 according to the well-known electro-optic effect to generate two sidebands (in the first order approximation) apart from the laser frequency with an interval of the modulation frequency.

A focusing lens 34 is positioned in the path of phase-modulated light beam 32. Lens 34 ensures that beam 32 is incident on an optical fiber positioner 36. Positioner 36 is a standard adjustable mechanical unit to hold the fiber and fix the orientation of the fiber in space. Positioner 36 is connected to an optical fiber 38. Preferably, fiber 38 is a single mode optical fiber at the wavelength of the light. Fiber 38 serves to guide phase-modulated light beam 32 to the vicinity of a process chamber 46. There, fiber 38 terminates in an optical fiber positioner 42 for emitting beam 32. A collimating lens 64 ensures that beam 32 is properly aimed at a first window 50 of chamber 46. Preferably, lens 64 is a gradient index lens which is attached to the end of the fiber. In particular, lens 64 ensures that beam 32 enters chamber 46 through window 50 and exits it through a second window 50'.

Process chamber 46 may be a vacuum coating chamber, an ion milling chamber, a sputtering chamber, a mass spectrometer chamber, or a vapor coating chamber. In this embodiment chamber 46 is a vapor deposition chamber with a sample 48. During deposition atoms 49 belonging to a coating material move through chamber 46.

A focusing lens 52 positioned past window 50' focuses light beam 32 emerging from chamber 46 on a photodetection device or photodetector 54. Photodetector 54 is a standard opto-electronic unit capable of responding to a high frequency signal. In the present embodiment, the detector has a band width of 1 GHz. Commonly available devices such as photomultiplier tubes, photodiodes, etc., can be employed as photodetector 54.

An amplifier 56 amplifies the detected signal from photodetector 54 from transmission line 72. Amplifier 56 is a standard electronic unit capable of amplifying radio-frequency signals.

A radio-frequency mixer 58 mixes the radio-frequency signal from source 44 through transmission line 66 and amplified signal from amplifier 56 through transmission line 72. Mixer 58 is a standard electronic unit working at radio frequencies.

A lock-in amplifier 60 processes the signal from mixer 58 through transmission line 68 by comparing with a reference signal from function generator 12 through transmission line 22 to output a signal related to the absorption. Lock-in amplifier 60 is a standard electronic unit capable of performing phase-sensitive detection.

A power controller 62 receives the absorption signal from lock-in amplifier 60 through transmission line 70 to control the power applied to sample 48 which is heated and evaporated by the applied power.

Atomic absorption apparatus 10 operates continuously during the technological process taking place inside chamber 46. In particular, light beam 16 with a predetermined polarization from laser 14 passes element 18 and polarization adjusting unit 20 and is delivered to modulator 30 through lens 24 and two mirrors 26 and 28. Modulator 30 is driven by radio-frequency source 44. The laser beam passing through modulator 30 is phase-modulated to generate two sidebands up and down from the laser frequency center with frequency interval of the modulation frequency. After modulator 30 laser beam is coupled into fiber 38 through lens 34 with the help of positioner 36. The laser beam is collimated through passing lens 64 and is directed, with the help of positioner 42, into chamber 46 through two windows 50 and 50', and then is coupled into detector 54 through lens 52. Meanwhile, sample 48 is evaporated by heating through power controller 62 to generate atoms 49 inside chamber 46. Power controller 62 is set at a desired value to apply a constant power to sample 48 when the loop is opened.

Phase-modulated laser beam passing through chamber 46 is absorbed by atoms 49. The absorption difference seen by the two sidebands generates a signal at detector 54. The signal is further pre-amplified by amplifier 56 and goes to mixer 58. Mixer 58 mixes the amplified signal from amplifier 56 and radio-frequency signal from source 44 to output a DC signal with information related to the atomic absorption. In present embodiment, the modulation frequency is smaller than the absorption resonance width, and the DC signal from mixer 58 is proportional to the slope of the line shape of the absorption at the laser frequency.

Simultaneously, the laser frequency is changed by applying a periodic wave form from function generator 12. Lock-in amplifier 60 compares the signal from mixer 58 and the reference signal from function generator 12 to output a DC signal proportional to the absorption at the laser frequency. This DC signal from lock-in amplifier 60 is used to control the power controller 62 by comparing this signal with the set value, when the loop is closed.

The above apparatus is accurate, functions without interruptions, and provides continuous feedback to adjust the deposition rate. This monitor is also versatile and low maintenance, since no part of it is directly exposed to the extreme conditions under which the deposition process takes place.

Moreover, this apparatus can be used to map the velocity profile of atoms inside chamber 46. Since the distribution of absorption vs. laser frequency relative to the absorption ferquency of a stationary atom represents the velocity distribution of the sample atoms, and different Doppler shifts correspond to different resonant frequencies, the Doppler shift is measured by comparing the resonance frequency with the frequency of the stationary atom. The spatial distribution of velocity or the velocity profile of the atoms is obtained when the spatial distribution of the Doppler shift is measured by changing the spatial position of the laser beam across the chamber windows through moving fiber and detector.

SUMMARY, RAMIFICATIONS, AND SCOPE

The presented atomic absorption apparatus using a phase-modulated light beam thus satisfies all objectives of the invention. Additionally, many changes and modifications can made to the apparatus without venturing beyond the scope of the invention. In one embodiment, lock-in amplifier is replaced by a computer for signal processing.

Also any laser source providing light of the required wavelength can be used.

This apparatus can be also used for any other particles including molecules and ions having absorption resonances accessible by the laser.

Therefore, the scope of the invention should be determined, not by examples given, but by the appended claims and their legal equivalents.

We claim:

1. An atomic absorption apparatus for measuring the absorption of a light beam having a characteristic frequency f by specific atoms, said atomic absorption apparatus comprising:

a) a laser for emitting said light beam, said light beam having a predetermined polarization;

b) a modulating signal source for generating and transmitting a modulating signal having a frequency larger than 50 MHz;

c) an electro-optic modulator located downstream from said laser for receiving said light beam and said modulating signal, and modulating said characteristic frequency f with said modulating signal to produce a phase-modulated light beam;

d) a domain comprising said specific atoms, said domain being located in the path of said phase-modulated light beam such that said phase-modulated light beam encounters said specific atoms when passing through said domain, whereby said specific atoms absorb a portion of said phase-modulated light beam depending on their motion relative to said phase-modulated light beam; and e) a photodetection means for receiving said phase-modulated light beam emerging from said domain and converting said phase-modulated light beam into an electrical signal.

2. The atomic absorption apparatus of claim 1, further comprising a polarization means positioned in the path of said light beam for altering said predetermined polarization of said light beam.

3. The atomic absorption apparatus of claim 2, wherein said polarizing means is a half-wave plate, such that said half-wave plate rotates said predetermined polarization.

4. The atomic absorption apparatus of claim 1, wherein said modulating signal source is a radio-frequency source.

5. The atomic absorption apparatus of claim 1, wherein said photodetection means is a device selected from the group consisting of a photodiode and a photomultiplier tube.

6. The atomic absorption apparatus of claim 1, further comprising an isolating means located in the path of said light beam for preventing the re-entry of said light beam into said laser, thereby ensuring substantially no deviations in said characteristic frequency f.

7. The atomic absorption apparatus of claim 1, wherein said domain comprises a chamber with a window for admitting said phase-modulated light beam inside said chamber and a window for allowing said phase-modulated light beam to exit.

8. The atomic absorption apparatus of claim 7, wherein said chamber is selected from the group consisting of a vacuum coating chamber, an ion milling chamber, a sputtering chamber, a mass spectrometer chamber, and a vapor coating chamber.

9. The atomic absorption apparatus of claim 1, wherein said laser is a tunable laser.

10. A method for measuring the absorption of a light beam having a characteristic frequency f by specific atoms, said method comprising the following steps:

a) emitting said light beam from a laser such that said light beam has a predetermined polarization;

b) generating and transmitting a modulating signal having a frequency larger than 50 MHz using a modulating signal source;

c) receiving said light beam and said modulating signal and modulating said characteristic frequency f with said modulating signal using an electro-optic modulator located downstream from said laser to produce a phase-modulated light beam; and d) passing said phase-modulated light beam through a domain comprising said specific atoms, said domain being located in the path of said phase-modulated light beam such that said phase-modulated light beam encounters said specific atoms when passing through said domain, whereby said specific atoms absorb a portion of said phase-modulated light beam depending on their motion relative to said phase-modulated light beam; and e) receiving said phase-modulated light beam emerging from said domain and converting said phase-modulated light beam into an electrical signal using a photodetection means.

11. The method of claim 10, further comprising the step of altering said predetermined polarization of said light beam using a polarization means positioned in the path of said light beam.

12. The method of claim 10, further comprising the step of preventing the re-entry of said light beam into said laser and the entry of stray light into said laser using an isolating means located in the path of said light beam.

13. The method of claim 10, further comprising the step of tuning said laser to adjust said characteristic frequency f.

14. The method of claim 10, further comprising the step of comparing the phase of said electrical signal with the phase of said modulating signal to produce a deviation signal.

15. The method of claim 14, comprising the step of determining the movement of said specific atoms in said domain using said deviation signal.

16. The method of claim 15, wherein said movement is represented in the form of a velocity profile.

17. The method of claim 10, further comprising the following steps:

a) generating an electrical reference signal corresponding to the intensity of said light beam;

b) comparing the magnitude of said electrical signal with said electrical reference signal to produce a difference signal.

18. The method of claim 17, comprising the step of determining the absorption of said phase-modulated light by said specific atoms in said domain using said difference signal.

19. An atomic absorption apparatus for measuring the absorption of a light beam having a characteristic frequency f by specific atoms, said atomic absorption apparatus comprising:

a) a laser for emitting said light beam, said light beam having a predetermined polarization;

b) a modulating signal source for generating and transmitting a modulating signal having a frequency larger than 50 MHz for modulating said characteristic frequency f of said laser to produce a phase-modulated light beam;

c) a domain comprising said specific atoms, said domain being located in the path of said phase-modulated light beam such that said phase-modulated light beam encounters said specific atoms when passing through said domain, whereby said specific atoms absorb a portion of said phase-modulated light beam depending on their motion relative to said phase-modulated light beam; and d) a photodetection means for receiving said phase-modulated light beam emerging from said domain and converting said phase-modulated light beam into an electrical signal.

* * * * *

UNITED STATES PATENT AND TRADEMARK OFFICE
CERTIFICATE OF CORRECTION

PATENT NO.   : 5,530,541
DATED        : June 25, 1996
INVENTOR(S)  : Charles H. Ahn, et al.

It is certified that error appears in the above-identified patent and that said Letters Patent is hereby corrected as shown below:

Column 1, line 3, insert the following:

This invention was made with Government support under contract F49620-95-1-0039 awarded by the Air Force Office of Scientific Research.  The Government has certain rights in the invention.

Signed and Sealed this

Twenty-first Day of December, 1999

Attest:

Q. TODD DICKINSON

*Attesting Officer*    *Acting Commissioner of Patents and Trademarks*